United States Patent
Blumenfeld et al.

(12) 
(10) Patent No.: US 6,228,580 B1
(45) Date of Patent: *May 8, 2001

(54) NUCLEIC ACID DETECTION METHOD USING NUCLEOTIDE PROBES ENABLING BOTH SPECIFIC CAPTURE AND DETECTION

(75) Inventors: Marta Blumenfeld, Paris; Michel Bouillot, Epinay sous Sénart, both of (FR)

(73) Assignee: Genset, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/000,384
(22) PCT Filed: Jul. 30, 1996
(86) PCT No.: PCT/FR96/01201
  § 371 Date: Jan. 30, 1998
  § 102(e) Date: Jan. 30, 1998
(87) PCT Pub. No.: WO97/05277
  PCT Pub. Date: Feb. 13, 1997

(30) Foreign Application Priority Data

Jul. 31, 1995 (FR) .................................................. 95 09290

(51) Int. Cl.[7] .............................. C12Q 1/68; C07H 21/02; C07H 21/04; C12N 15/00
(52) U.S. Cl. ........................... 435/6; 536/23.1; 536/24.3; 935/76; 935/77
(58) Field of Search ................................ 435/6; 536/23.1, 536/24.3; 935/76, 77, 78

(56) References Cited

U.S. PATENT DOCUMENTS

| 4,775,619 | * | 10/1988 | Urdea ........................................ 435/6 |
| 4,868,105 | | 9/1989 | Urdea et al. . |
| 5,512,439 | * | 4/1996 | Hornes et al. ............................ 435/6 |
| 5,629,158 | * | 5/1997 | Uhlen ........................................ 435/6 |
| 5,670,316 | * | 9/1997 | Sena et al. .............................. 435/6 |
| 5,786,203 | * | 7/1998 | Lovenberg et al. .............. 435/252.3 |
| 5,817,512 | * | 10/1998 | Morrow et al. .................... 435/320.1 |

FOREIGN PATENT DOCUMENTS

| 13038/95 | 12/1993 | (AU) . |
| 0 622 464 A2 | 11/1994 | (EP) . |
| WO 94/26934 | 11/1994 | (WO) . |
| WO 95/11316 | 4/1995 | (WO) . |
| WO 95/16055 | 6/1995 | (WO) . |

OTHER PUBLICATIONS

Aubert et al., J. of Histochemistry and Cytochemistry 41(7) : 1099–1103 (1993).*
The Stratagene Catalog, p. 39 (1988).*
Matthews et al., Analytical Biochemistry 169 :1–25 (1988).*
Aubert et al., The Journal of Histochemistry and Cytochemistry 41(7) : 1099–1103 (1993).*
Kessler, C., "The digozigenin: anti–digoxigenin (DIG) technology a survey on the concept and realization of a novel bioanalytical indicator system," *Molecular and Cellular Probes*, 5: 161–205 (1991).
Viaene, A. and Baert, J., "*In Situ* Hybridization of DIG–labeled RNA Probes in a Study of Cytokeratin Expression in Human Esophageal Epithelium," *Boehringer Mannheim*, pp. 13–15 (Jan./1994).
"PCR ELISA," *Boehringer Mannheim*, pp. 4–5 (Jan./1994).

\* cited by examiner

*Primary Examiner*—Ethan Whisenant
(74) *Attorney, Agent, or Firm*—Knobbe, Martens, Olson & Bear, LLP

(57) ABSTRACT

A nucleic acid detection assay is disclosed which assay comprises hybridizing a large nucleic acid probe (i.e. preferably more than 100 bp long) with a RNA or DNA target nucleic acid present in a biological sample. The probe in this method is to comprise both a detection element and a capture element and is to to be degradable by a suitable enzyme when it is single stranded. Following hybridization the sample is treated with a enzyme capable of degrading unhybridized nucleic acids. Then the hybrids are captured by contacting them with a solid support comprising an element capable of binding with the capture element of the probe. Finally the detection element of the probe is used to detect the probe, thereby indicating that the target nucleic acid is present in the biological sample.

25 Claims, 8 Drawing Sheets

FIG_1A

FIG_1B

FIG_2A

FIG_2B

FIG_3A

FIG_3B

FIG_5

FIG_6

FIG_7

FIG_8

FIG_9

FIG_10

NUCLEIC ACID DETECTION METHOD USING NUCLEOTIDE PROBES ENABLING BOTH SPECIFIC CAPTURE AND DETECTION

This application is a 371 of PCT/FR96/01201 filed Jul. 30, 1996.

The present invention relates to a method for detecting nucleic acids using nucleotide probes permitting both specific capture and detection. The present invention permits automation of the large-scale specific detection of nucleic acids using a single-stranded ribonucleotide probe complementary to a target nucleotide sequence, said probe permitting both capture on a suitable surface and rapid and sensitive detection.

As a result of the major genome sequencing and analysis programmes, biology some years ago entered a new era, that of the massive acquisition of data based on the intensive use of improved existing techniques. In five to ten years time, the genome of several model organisms, as well as the human genome, will be completely sequenced. Since the number of genes encoded by the human genome is calculated at between 50,000 and 100,000, several thousand sequences of coding regions (cDNA) and also of regulatory regions (promoters) will have to be listed, analyzed and integrated in databases, and their expression profiles in some hundred tissues or cells will be able to be established.

The expression profile of a gene consists in studying the relative abundance of the corresponding messenger RNA (mRNA) expressed in particular cells (for example belonging to different tissues, or representing different stages of development, particular pathologies, induction by drugs, and the like). Establishment of the expression profiles of genes hence requires the specific and sensitive detection of mRNAs.

The detection of specific mRNAs may be undertaken by two different types of approach: those based on amplification techniques and those based on hybridization techniques.

The use of amplification techniques such as RT-PCR (reverse transcriptase-polymerase chain reaction) appears to be of limited applicability in a planned large-scale study of mRNA expression profiles on account of the cost which would be entailed in synthesizing the large number of oligonucleotides needed for carrying it out (for 50,000 different genes, the minimum number would be 100,000 oligonucleotides).

The "sandwich" hybridization technique described for the first time by Dunn A. R. and Hassell J. A. (1977, cell, 12, 23–36) was developed in order to avoid the purification and immobilization of target nucleic acids which formerly necessitated detection after solid-phase hybridization. This technique is based on the existence of two nonoverlapping probes directed against the same target nucleic acid. The first probe is immobilized on a solid surface and permits capture of the target. The second probe possesses a tracer in its sequence and permits detection of the target. This technique is essentially used for the detection of amplification products. In actual fact, the probes used are small (from 20 to 25 nucleotides) and, unlike long probes, they do not enable strong hybridization signals to be obtained. This technique is unsuitable for the simultaneous detection of a large number of targets, since each probe necessitates hybridization temperatures which can be different.

The second approach is based on hybridization techniques that do not involve amplification, and which hence require great sensitivity. There are several formats which may be used to detect a specific hybridization: liquid-phase hybridization; solid-phase hybridization; in situ hybridization on tissues or cell bodies. In all cases, the probe is a nucleic acid (DNA or RNA) capable of hybridizing with a complementary nucleic acid sequence: the target (DNA or RNA). The kinetics of the different nucleic acid hybridization reactions are well known (Britten et al., 1974, Methods Enzymol, 29, p. 363; Kohme et al., 1977 Biochemistry, 16 pp. 5329–5341), and knowledge of the parameters involved in the rate of hybridization as well as in the stability of the target-probe hybrids enables the optimal conditions to be determined for obtaining the best signal-to-background ratio.

Liquid-phase hybridization is very efficient and has the advantage of affording the fastest rate of hybridization. However, it is difficult to separate the free probe from the hybridized probe. Solid-phase hybridization methods which involved immobilization of the target (or of the probe) on a solid surface (e.g. nitrocellulose, nylon) are easier to carry out from the standpoint of separation of the unhybridized probe. However, compared to hybridization in solution, the rate of hybridization is from 7 to 10 times as slow. Lastly, in situ hybridization permits the microscopic examination of DNA or RNA sequences present in cells or tissues while preserving their localizations. This method is suited to cytology or histology laboratories.

In the specific case of the detection of RNAs, the so-called "northern blot" solid-phase technique constitutes the most widely used hybridization method, used both in medical analysis and in basic research. Northern blotting, while it is the only method capable of providing information about the size of messengers, and hence about the identity of the target, cannot be considered for large-scale analyses because of its low sensitivity and difficulties of automation. For similar reasons, the in situ hybridization technique likewise appears to be unsuitable for large-scale studies of RNA expression profile.

Among the methods of detection of RNA based on hybridization in solution, the nuclease protection technique has the advantage of being a very sensitive and specific method. In this technique, single-stranded RNA or DNA radioactive probes are hybridized in solution with RNA preparations containing the target RNA. After hybridization, the unhybridized nucleic acids (both the unhybridized probe and the RNAs of the preparation) are degraded by the action of nucleases specific for single-stranded nucleic acids (in general, RNases A and T1 for RNA probes, and nuclease S1 for RNA or DNA probes). The hybridization of the probe with its complementary RNA target "protects" the probe from degradation by the nuclease, and results in double-stranded molecules whose length is defined by the probe-target complementarity.

On the other hand, nonspecific hybridization of the probe with RNAs other than the target results in double-stranded molecules which are shorter than those originating from the specific hybridization. The two types of products, specific and nonspecific, may hence be distinguished according to size, the most usual analysis being polyacrylamide gel electrophoresis. An alternative technique of analysis by chromatographic separation has been proposed in WO 95/113116.

While the nuclease protection technique has the advantage of being sensitive and specific, the analytical method consisting of an electrophoretic or chromatographic separation is incompatible with automation of the method and use of a large number of samples.

The present invention is designed to permit specific detection of nucleic acids, in particular of RNA, in a format which makes it possible to handle simultaneously a large number of samples by a procedure which can be fully automated, while being sensitive, specific a reproducible.

Another object of the present invention is, in particular, to provide a method which permits the specific detection of mRNAs from total RNAs.

The invention is based on the use of a method of hybridization in solution of nucleic acids with a nucleotide probe which, in addition to a specificity of recognition brought about by its sequence, possesses modifications which enable it to accomplish two different functions. The first function permits binding to a solid support of the probe-target hybrid, or of the probe originating from a previously denatured probe-target hybrid. The second function of the probe permits specific detection by radioactive or cold detection methods.

Generally speaking, the invention involves a methodology comprising:

(1) a hybridization in the liquid phase using a doubling labeled nucleic acid probe that hybridizes specifically with a given RNA or DNA.

(2) a degradation by nucleases of the unhybridized nucleotide sequences.

(3) separation of the hybrids by specific capture on a solid support of the hybrids formed, by means of a modification of the probe.

(4) detection of the hybrids as a result of the abovementioned modification, or by means of another modification present on the probe.

More specifically, the subject of the present invention is a method for detecting nucleic acids, characterized in that it entails the following steps:

a) hybridization is carried out in solution of a large nucleic acid probe, in particular one having more than 100 nucleotides, capable of hybridizing with a given RNA or DNA in a sample containing nucleic acids, said probe comprising detection components and first capture components on a solid support;

b) degradation of the unhybridized nucleotide sequences in the sample is carried out with an enzyme that degrades unhybridized nucleic acids, c) capture of the hybrids obtained in step b) is accomplished by bringing them into contact with a solid support coated with the second capture components that interact with said first capture components of said probe, and d) detection of the hybrids, or of the probes originating from the hybrids after denaturation, is accomplished by means of said detection components.

The use of large probes, in particular ones having more than loo nucleotides, confers greater specificity of hybridization and the possibility of introducing sufficient modifications for the detection and capture of the probe while preserving the stability of the hybridization.

In particular, the probe contains from 100 to 1000 nucleotides, preferably from 250 to 500 nucleotides.

One aspect of the invention is associated with the use, after incubation with nucleases, of one or more techniques of removal of oligonucleotides (less than 100 bases), such as differential precipitation, filtration through membranes, gel filtration (exclusion chromatography) or any other technique permitting separation of the target-probe hybrids from the degradation products of nucleic acids, in particular of the unhybridized probe.

In general the two functions of the probe are accomplished by two different nucleotide modifications. However, it should be noted that the same modification may be used for capture and for detection.

According to the present invention the probe comprises a sufficient amount of detection components and of capture components to effect capture and then a sufficient detection. However, the amount of said detection components and of said first capture components bound to the probe is optimized in order to be compatible with the hybridization of step a) and the nondegradation of the hybrids in step b).

It should be borne in mind that the introduction of modified nucleotides into the bifunctional probes can cause a destabilization of the specific hybrids in respect of the pairings close to the modifications. It emerges, in effect, from the examples illustrating the invention which are described below that, if the amount of the modifications of the probe is too large, the hybridization is insufficiently stable, so that even the hybrids can become degraded by the enzymes used in step b).

Preferably, when the detection components and first capture components are biological molecules substituted on nucleotides constituting the probe, the latter should not contain more than 15%, preferably not more than 10%, of nucleotides modified with said detection components and said first capture components. It will also be understood that these amounts are dependent on the size of the molecules constituting the detection components and capture components. If the steric hindrance is too great, they will weaken the stability of the hybridization.

The nucleotide probes according to the present invention can be DNA probes or, preferably, RNA probes. The RNA probes can be obtained by in vitro transcription and possess some advantages over DNA probes. RNA probes occur directly in the form of a single strand, so they do not require denaturation. Moreover, there is no interference with a complementary strand as in the case of DNA probes. Thus, RNA probes form more stable hybrids with their targets than those obtained with DNA probes.

Advantageously, to detect an mRNA expressed from a given gene, an RNA probe obtained by in vitro transcription of cloned cDNA fragments of said gene is used.

Advantageously, an RNA probe obtained by in vitro transcription using nucleotides, some of which are modified by coupling to a said detection component and/or a said capture component, is used.

Numerous modifications may be incorporated in the RNAs transcribed by the RNA polymerases SP6, T3 and T7. For example, ribonucleotides containing biotin groups (such as biotin-UTP and DIG-UTP) or fluorescein groups (such as F1-11-UTP, F1-12-UTP) exist, which can replace UTP in the in vitro transcription reactions catalyzed by the RNA polymerases SP6, T3 or T7. In addition, other types of modifications may be incorporated in ribonucleotides according to the techniques known to a person skilled in the art.

After hybridization of the bifunctional probe with the preparation containing the target RNA, the unhybridized probe has to be degraded under conditions which do not bring about a degradation of the specific probe-target hybrids. The method chosen to remove the unhybridized probe must also take account of the possible existence of single-stranded regions in the probe-target hybrid, in order not to lose a portion of the specific signal. There are several enzymes which have the capacity to hydrolyze single-stranded nucleic acids specifically. Among others, there may be mentioned nuclease S1, mung bean nuclease or exonuclease VII, which do not have sequence specificity, and RNase A, RNase CL3, RNase Phy M, RNase T1 or RNase U2, which cut only upstream and/or downstream of certain nucleotides. The use of one or more nucleolytic enzymes which are specific for single-stranded regions and are not specific for the modified nucleotides incorporated in the probe form part of the invention. For example, if the riboprobes contain modifications linked to UTP, RNase T1 (which cuts on the 3' side of G) and/or RNase CL3 (which cuts on the 3' side of C) and/or RNase U2 (which cuts on the 3' side of A) should preferably be used so as to decrease the probability of cutting around the modified UTPs in the probetarget hybrid.

Advantageously, when mRNAs are detected, in step a) an RNA probe is used, and in step b) the enzymatic degradation is carried out with an RNase.

When the detection components and said first capture components are substituted on given nucleotides, it is preferable to use in step b) an enzyme which couples the single-stranded nucleic acids at a nucleotide other than said substituted nucleotides.

In particular, the detection components and said first capture components are substituted on Uridine nucleotides and the enzyme of step b) is an RNase $T_1$.

The capture group permits specific binding of the probe to the solid phase.

In one embodiment, said first capture components of said probe consist of a first biological molecule bound covalently to said probe and said second capture components of said solid support consist of a second biological molecule bound to the solid support, which second biological molecule interacts and binds noncovalently to said first molecule.

Special mention may be made of the embodiment in which said first and second molecules constitute the biotin/streptavidin system or antigen/antibody system, or still more especially the first and second capture components can be the system comprising digoxigenin (DIG) and anti-DIG antibody or fluorescein and an anti-fluorescein antibody; more generally, any ligand-receptor or hapten-antibody system.

According to the invention, the capture of the probe-target hybrid nucleic acids, or of the probe originating from a previously denatured probe-target hybrid, takes place on a solid surface. This surface is preferably, but is not limited to, a microplate. Capture can take place on the surface of a plasma resonance detector (Surface plasmon resonance Fisher et al. 1994, Curr. of Biotech. 5, 389–395). The surface chosen permits specific binding of the probe as a result of the immobilization of the molecules having a high affinity for the capture groups present in the probe.

The detection group permits specific demonstration of the probe. For example, biotin may be recognized by streptavidin or by an anti-biotin antibody coupled to an enzyme; DIG by anti-DIG antibodies coupled to an enzyme, or fluorescein by anti-fluorescein antibodies coupled to an enzyme. The detection may also be mediated by the presence of a radioactive nucleotide in the probe.

The detection component of the probe can be a component which is directly or indirectly detectable. In effect, "detection component" is understood to mean a molecule which can be detected directly or indirectly, that is to say, in the latter case, after binding by interaction or covalent coupling with another molecule and/or a solid particle. "Direct detection" is understood to mean, in particular, the cases where said molecule itself contains a detectable component such as a radioactive or fluorescent component, or where said molecule is coupled to an enzyme which can be detected using a substrate or alternatively said molecule is coupled to a fluorescent molecule. "Indirect detection" is understood to mean, in particular, the cases where said molecule is a biological molecule capable of reacting physico-chemically by a noncovalent interaction or by covalent coupling with another biological molecule itself containing a directly detectable component such as a radioactive or fluorescent atom, an enzyme or a fluorescent molecule.

The indirectly detectable detection component can consist of a biological molecule capable of reacting noncovalently with another biological molecule containing a directly detectable component such as an enzyme. The streptavidin/biotin or antigen/antibody systems may be mentioned especially. In particular, the indirectly detectable detection component is chosen from biotin, fluorescein and DIG.

In the case of radioactive detection, the presence of a radioactive nucleotide in the probe can be, for example, discerned by counting in a detector of radioactivity suitable for microplates. In the case of cold detection, the detection group incorporated for this purpose in the probe may be recognized using a specific ligand/antibody conjugated to an enzyme, followed by incubation with a substrate. Thus, biotin may be recognized by streptavidin or by an anti-biotin antibody coupled to an enzyme; DIG by anti-DIG antibodies coupled to an enzyme, or fluorescein by anti-fluorescein antibodies coupled to an enzyme. The enzymes used for cold detections can be, inter alia, alkaline phosphatase, peroxidase or b-galactosidase. There are numerous colorimetric, fluorescent or chemiluminescent substrates for these enzymes. The measurement of enzyme activity may be carried out by automatic reading in a colorimeter, fluorimeter or luminometer suitable for microplates.

Alternatively, if the chosen capture surface is that of a plasma resonance biosensor, the presence of detection groups in the probe may be determined by direct measurement of the interaction with specific ligands/antibodies.

When the capture and detection components are biological molecules substituted on a nucleotide, in particular Uridine, biotin, fluorescein or digoxigenin may be mentioned as detection and/or capture component. More especially, the detection component is digoxigenin and/or biotin and said first capture component is chosen from biotin and digoxigenin, respectively. In one embodiment, said first capture component is biotin or digoxigenin, and nucleotides carrying these modifications are Uridines and said detection component is DIG or biotin, respectively.

Preferably, the detection group is DIG, the conjugate is an anti-DIG antibody coupled to alkaline phosphatase and the substrate permits a chemoluminescent detection.

In one embodiment illustrated by the examples of the detailed description which follows, the probe contains from 2 to 5% of the nucleotides modified by coupling to a said detection component consisting of a biotin molecule, in particular 3 to 4%, and from 2 to 5% of the nucleotides modified by coupling to a said first capture component consisting of a digoxigenin molecule, in particular 2 to 3%.

The subject of the present invention is also a diagnostic method in which a detection method according to the present invention is used, comprising the detection of nucleic acids involved in a pathology.

The subject of the present invention is also a kit which is useful for carrying out a detection or diagnostic method according to the present invention, characterized in that it contains large RNA probes, in particular ones having more than 100 nucleotides, carrying detection components and said first capture components on a solid support, and a solid support coated with said second capture components.

Other features and advantages of the present invention will become apparent in the light of the description and the examples which follow, reference being made to FIGS. 1 to 10.

FIG. 1 A depicts the results for the binding of 1 fmol of (32aP) CTP-labeled biotin-DIG riboprobe, and enables the percentage of biotin introduced for incorporated in the riboprobe which is necessary for good binding to a plate to be determined. The riboprobes studied are obtained by reverse transcription using a variable proportion of biotin-UTP (5, 10, 15, 25, 100%) and a fixed amount of DIG-UTP (10%). The detection of the riboprobes is performed by measurement of the radioctivity.

The riboprobes studied consist of DIG-UTP (0, 5, 15, 25 and 35%). They are radiolabeled with ($\alpha$-$^{32}$P) CTP.

Each riboprobe is hybridized with a complementary ribonucleotide sequence (10 or 1 ng) in the presence of 10 $\mu$g of yeast RNA (+). A control without digestion by Rnase T1 (−) and an RNase control without a complementary probe (0) were performed for each probes.

The two radiolabeled riboprobes used at 1 fmol (45,000 cpm) were placed with a decreasing amount of a cold complementary ribonucleotide sequence (subjected to tenfold serial dilutions from $10^4$ to $10^3$ pg) in the presence of 10 $\mu$g of yeast RNA (+). A probe control without digestion by Rnase T1 (−) and an RNase control without a complementary probe (0) were performed for each probes. The band visible on the gel corresponds to the riboprobe which has not been degraded (since in hybrid form) on the digestion with Rnase T1.

FIG. 7 depicts the autoradiograph of a polyacrylamide gel. It shows the detection of the messenger of the $\beta$-actin gene in different human or rat cells using a riboprobe (complementary to a 250 nucleotides of the messenger of the mouse $\beta$-actin gene) consisting of 15% of biotin-UTP and 10% of DIG-UTP and radiolabeled with ($\alpha$-$^{32}$P) CTP. The order of the different cells or tissues tested is: brain (rat), kidney (rat), liver (rat), Jurkat (human), HepG2 (human), H4II (rat), placenta (human), yeast, Hela (human). For each sample, a control of the riboprobe without Rnase T1 (−) and a detection of the mRNA of the $\beta$-actin gene (+) were carried out. Control of the specificity of the reaction is carried out using yeast.

The detection of the presence of the riboprobe is carried out after cutting out the wells and counting the radioactivity on a Beckman LS6000IC counter. The $\beta$-actin mRNA is tested for in 10 $\mu$g, 5 $\mu$g and 1 $\mu$g of total RNAs extracted from different tissues (see legend).

In the examples, modified riboprobes obtained by transcription from nucleotide monomers designated NTP, comprising modified nucleotides UTP-biotin (Boehringer, Ref. 1388908) andUTP-DIG (Boehringer, Ref. 1209256), are used.

When it is stated that riboprobe is obtained from n% of biotin-UTP or DIG-UTP, this means that the percentage of biotin-UTP relative to the total amount of modified and unmodified UTP used for the transcription is n%. This corresponds to a percentage of corresponding modified nucleotide in the riboprobe obtained of approximately n/4%.

Example 1 shows the bifunctional aspect of the biotin-UTP and DIG-UTP riboprobes. Example 2 underlines the importance of the degree of modification in relation to the test of protection from digestion by ribonucleases RPA. Example 3 illustrates an application of the invention as a method for the detection of gene expression.

EXAMPLE 1

DEMONSTRATION OF THE CAPTURE AND DETECTION OF A RIBOPROBE CONSISTING OF BIOTIN-UTP AND DIG-UTP ON A MICROPLATE

With the projects relating to the sequencing of the human genome, a considerable effort has been expended in relation to the automation of DNA sequencing methods. However, the traditional methods of analysis of gene expression are not suited to the detection of an ever increasing number of messengers. Thus, a major advantage of a new method for detecting messenger RNAs lies in its potential for automation. And must be able to be carried out on a solid support such as a microplate, which is especially suitable for studying large series of samples. The use of a riboprobe possessing a functional portion permitting, on the one hand its capture, and possessing a property of specific recognition is seen to be very suitable for the detection of messenger RNAs. In the example presented, the capture is effected by biotin and the detection by DIG.

1. General Principle of the use of a Riboprobe.

A DNA segment corresponding to a portion of a gene is inserted at a cloning site immediately downstream of a bacteriophage (T3, T7 or SP6), RNA polymerase promoter, in an orientation which leads to the production of an antisense RNA. The recombinant plasmid is then cut with a restriction enzyme on the 3' side of the insert. The linearized plasmid is then transcribed in the presence of ribonucleotides comprising modified ribonucleotides, for example biotin-UTP and DIG-UTP. An excess of this doubly labeled RNA is hybridized in solution with the mRNAs to be tested. The hybridizations are carried out under standard stringent conditions at T=40–50° C., overnight (16 hours) in an 80% formamide, 0.4 M NaCl buffer at a pH of between 7 and 8. The unhybridized probe is then eliminated by digestion using ribonucleases specific for single-stranded RNA, such as the RNases CL3, T1, Phy M, U2 or A. The presence of the first modification, for example biotin-UTP, in the mRNA:riboprobe (biotin-DIG) hybrid enables it to be captured on a microtitration plate whose surface is coated with streptavidin. The presence of another modification, for example DIG, enables the hybrid to be detected and quantified by an ELISA method using an anti-DIG antibody coupled to alkaline phosphatase. Moreover, it is also possible to carry out a transcription in the presence of $(\alpha\text{-}^{32}P)$ CTP in order to be able to detect and quantify the hybrid (mRNA:riboprobe) after application to a plate.

2. Model System: HNF1 (hepatic nuclear factor 1)

A 490 bp PvuII fragment of a cDNA coding for rat HNF1 (992 to 1482, Chouard et al. 1990, NAR 18, 5853–5863) is subcloned at the SmaI site of the vector pBS (Stratagene). The antisense riboprobe is obtained after linearization of the vector by cleavage with EcoR1, followed by a transcription carried out with T3 RNA polymerase. Synthesis of the sense riboprobe is accomplished after cleavage of the vector with HindIII, followed by a transcription with T7 RNA polymerase.

3. Synthesis of the Riboprobe

Each transcription reaction with T7 or T3 RNA polymerase is carried out in an Eppendorf tube with the following conditions: DEPC H20 q.s. 20 µl; 40 mM Tris-HCl pH 7.5; 6 mM MgCl2; 2 mM spermidine; 5 mM NaCl; 10 mM DTT; 100 µg/ml bovine serum albumin (BSA) (fraction V, Sigma); 500 µM CTP, ATP, GTP; variable amounts of UTP, biotin-UTP and DIG-UTP, depending on the desired percentage of modification (for example, to obtain a 15% biotin and 10% DIG riboprobe: 75 µM biotin-UTP; 50 µM DIG-UTP, 375 µM UTP); 1 U/ml of ribonuclease inhibitor; 40 U of T7 or T3 RNA polymerase; 1 µg of plasmid DNA linearized after digestion with a suitable restriction endonuclease (EcoR1 or Hind III). The mixture is incubated for 2 hours at 37° C. When transcription is complete, the plasmid DNA is digested by adding 1 µl (1 unit) of DNase RQ1 (Promega). The reaction is incubated for 15 minutes at 37° C. The unincorporated ribonucleotides are removed by passage through a Biospin 30 exclusion chromatography column (Biorad).

In order to quantify the synthesis of the riboprobe or determine the presence of a hybrid (mRNA:riboprobe) radioactively, the transcription is carried out with 1–7 µl of (a32P)CTP (800 Ci/ml; 20 mCi/ml), depending on the desired specific activity. The quality of the riboprobe is determined by migration on a 5% acrylamide electrophoresis gel under denaturing conditions.

4. Capture of the Riboprobes on Microplates

Microplate wells linked to streptavidin (Boehringer 1602853) are covered with 100 µl of hybrid diluted in 1×PBS buffer; 1% BSA (bovine serum albumin) for 1 hour at 37° C. The plates are then washed 5 times with washing buffer: 0.1 M NaCl; 0.1 M Tris-HCl; 0.1% Tween 20; 3 mM MgCl2, pH 7.5. 100 µl (70 mU) of anti-DIG antibody coupled to alkaline phosphatase (Boehringer) are then added and incubated for 1 hour at 37° C. in washing buffer containing 1% BSA.

5. Detection of the Riboprobes on Microplates

Depending on the modification of the probe, the detection can be cold (fluorescent or luminescent) or radioactive.
5.1. Fluorescent Detection The reaction is carried out with 100 µl of 4-methylumbelliferyl phosphate (Sigma) substrate at a concentration of 0.4 mg/ml in 0.1 M diethanolamine buffer, pH 9.8. Incubation is carried out overnight at room temperature. Measurement of the fluorescence is carried out with a fluorimeter (Dynatech) with an excitation wavelength of 365 nm and an emission wavelength of 450 nm.
5.2. Luminescent Detection The reaction is carried out with 100 µl of AMPPD substrate (Tropix) diluted to 1/59 in the presence of Sapphire enhancer (Tropix) diluted to 1/10 in 0.1 M diethanolamine buffer, pH 9.8. The measurement of the luminescence is carried out after 20 minutes at room temperature on a Micro Beta Trilux luminometer (Wallac).
5.3 Radioactive Detection This involves the use of radiolabeled riboprobes. After being cut out, each well is brought into contact with 3 ml of scintillation fluid. The measurement of the radioactivity is carried out on a Beckman LS6000IC counter.

6. Results

Biotin-UTP was incorporated in the riboprobe, which enables it to be captured specifically by streptavidin previously immobilized on a microplate.

For all the plate binding studies a radiolabeled riboprobe not possessing biotin-UTP in its sequence was used as a control of specificity.

6.1 Influence of the Percentage of Biotin on the Degree of Capture of a Single-stranded Riboprobe.

Figure 1A:
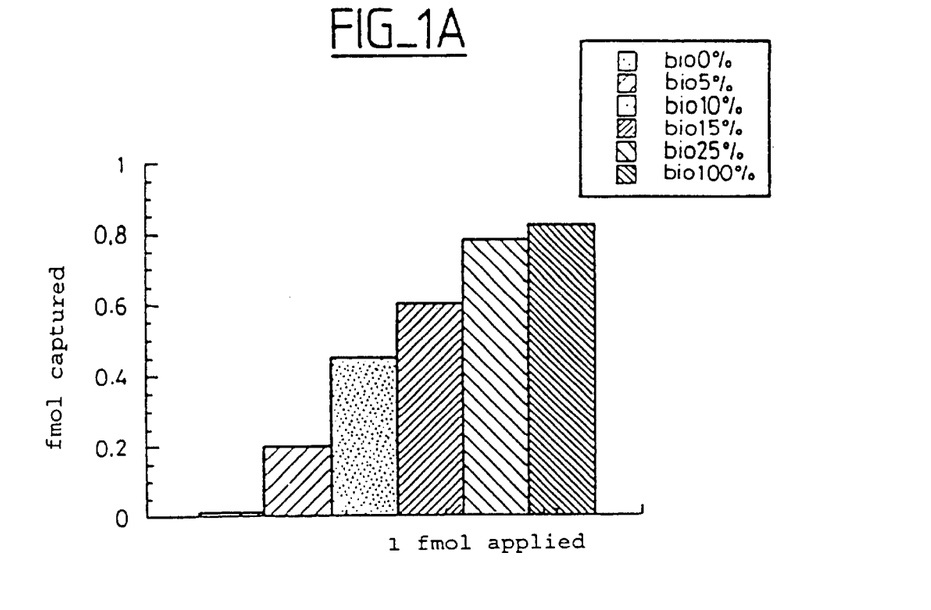

As shown in FIG. 1A, the capture of the single-stranded riboprobe (biotin-UTP, (a32P) CTP) is correlated with the amount of biotin incorporated in the riboprobe. The smallest binding was obtained with 5% of biotin. Then increases linearly up to 25% of biotin, to reach a plateau. The detection is carried out by measurement of the radioactivity. When a riboprobe containing 100% of biotin-UTP is used, the maximum degree of capture is 80%.

Figure 1B:
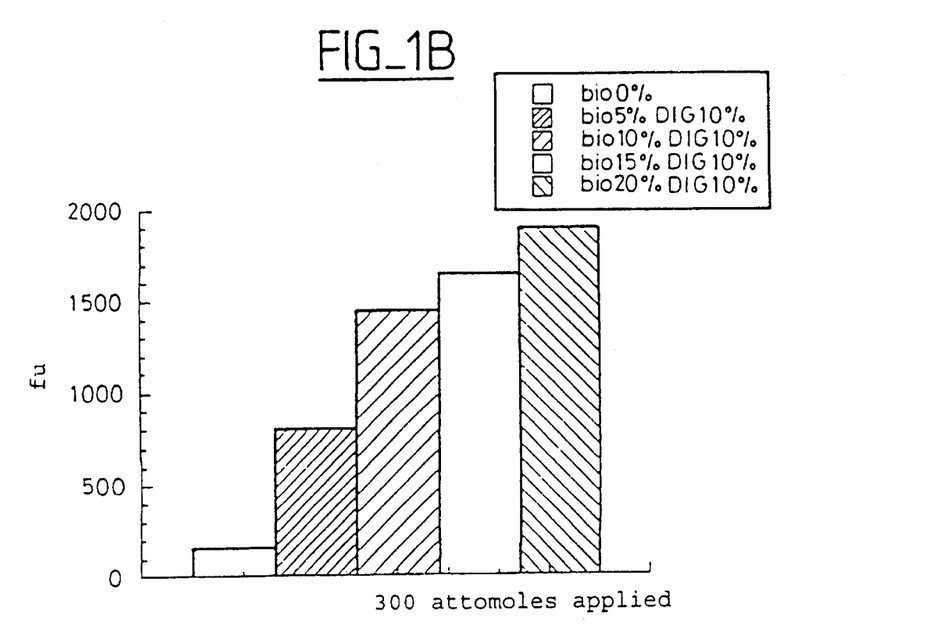
FIG. 1B depicts the detection of 300 amol of riboprobes using anti-DIG antibody (cold detection system). The riboprobes studied are formed from a varible percentage of biotin-UTP (5, 10, 15, 25%) and 10% of DIG-UTP.

The influence of the percentage of biotin-UTP on the degree of capture may also be discerned with a cold detection system. However, it is necessary to incorporate DIG-UTP in the riboprobe. FIG. 1B shows such a detection system. In agreement with the above results, the degree of capture increases with the percentage of biotin-UTP.

6.2. Threshold of Sensitivity of the Different Detection Systems.

Different types of detection may be used, radioactive or cold.

Radioactive detection is carried out after the incorporation of a ribonucleotide radiolabeled with (a32P) UTP or (A32P) CTP.

Cold detection is possible as a result of the incorporation of a modified nucleotide such as biotin, digoxigenin or fluorescein, detected with a conjugate consisting of a specific ligand (streptavidin for biotin) or a specific antibody (anti-biotin, anti-DIG, anti-fluorescein) coupled with an enzyme (alkaline phosphatase, peroxidase). Visualization is carried out by measuring the appearance of a fluorescent or luminescent product.

Hereinafter, the detection is carried out either by the incorporation of a radioactive nucleotide (A32P) CTP, or by the incorporation of DIG-UTP followed by a measurement of fluorescence or of chemiluminescence.

Figure 3A:
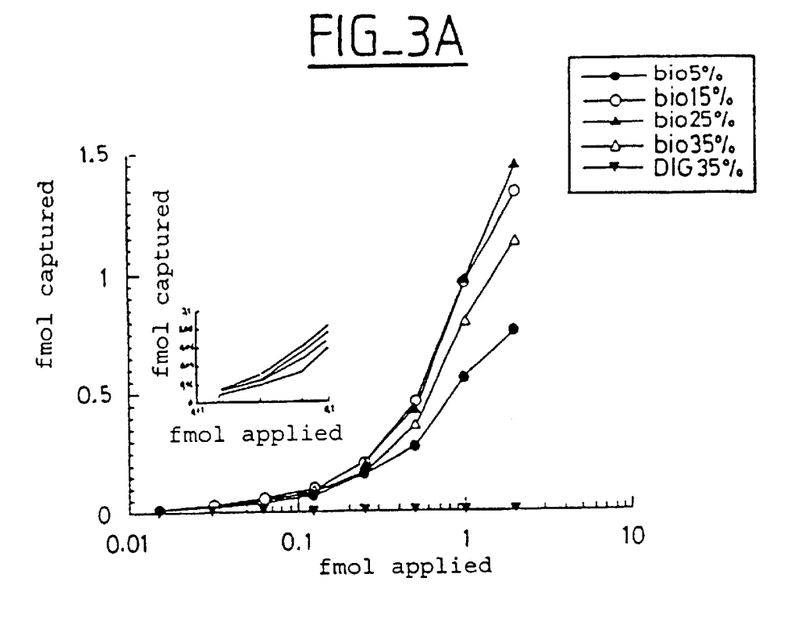
FIG. 3A depicts the capture of riboprobes (biotin-UTP) hybridized with an ($\alpha$-$^{32}$P) CTP-labeled complementary nucleotide sequence. This enables the binding of the riboprobes in double-stranded form to be studied. The riboprobes studied are prepared from a variable percentage of biotin-UTP (5, 15, 25, 35%). The hybrids are subjected to doubling dilutions from 2 to 0.015 fmol. The detection of the hybrids is performed by measurement of the radioactivity. These curves show the optimum amount of biotin-UTP in the riboprobe (in double-stranded form) for obtaining good binding.

In the case of radioactive detection, to obtain the greatest possible sensitivity, riboprobes having a high specific activity ($2 \times 10^5$ cpm/fmol) were used. Under these conditions, FIG. 3A shows that it is possible to detect up to 1 attamole of riboprobe on the plate.

For cold detection, as in radioactive detection, the threshold of sensitivity depends on the level of incorporation of the modified nucleotide used for detection (DIG-UTP).

Figure 2A:
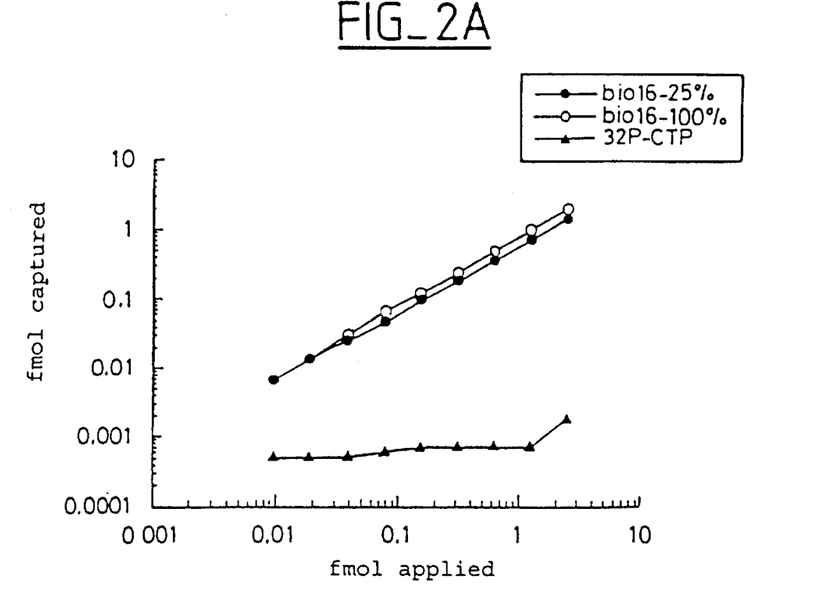
FIG. 2A shows the binding of ($\alpha$-$^{32}$P) CTP-labeled biotin-UTP (25 and 100%) riboprobes with a high specific activity ($2 \times 10^5$ cpm/fmol). This enables the sensitivity of the binding to be determined more precisely. The riboprobes undergo doubling dilutions from 2.5 to 0.01 fmol.
Figure 2B:
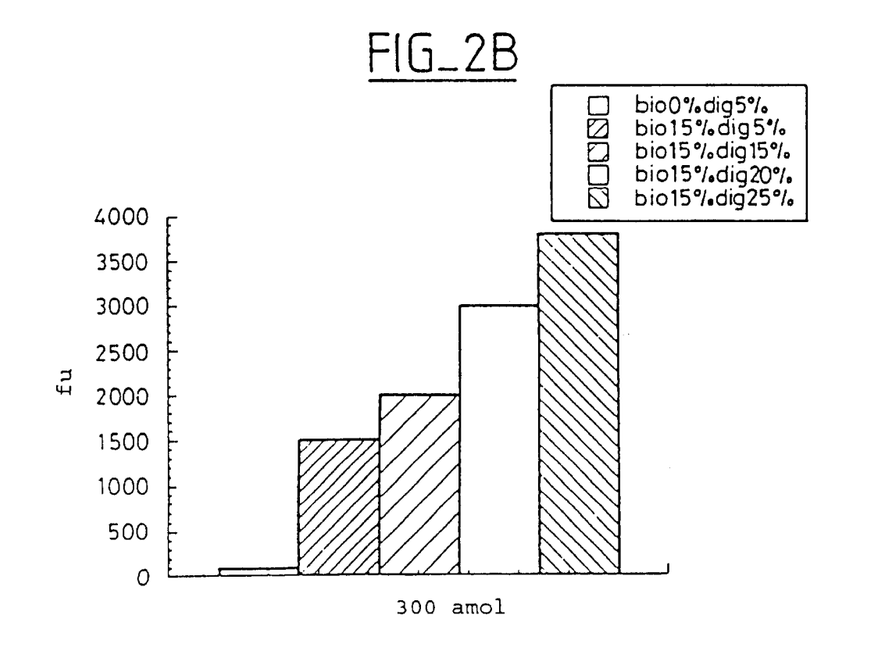
FIG. 2B shows the results for the detection of biotin-DIG riboprobes as a function of the percentage of DIG in the riboprobe, using an anti-DIG antibody coupled to alkaline phosphatase followed by measurement of fluorescence.

For example, FIG. 2B shows that the intensity of the signal increases with the percentage of DIG-UTP present in the riboprobe: a probe consisting of 25% of DIG-UTP is detected with 2.5 times the intensity of a probe having 5% DIG-UTP. Under conditions of incorporation of DIG-UTP corresponding to the detection maximum (35% DIG-UTP), the threshold of detection is 10 attamoles in fluorescence and 5 attamoles in luminescence.

These results show that it is possible to detect with different systems (radioactive or cold) riboprobes captured on microplates. In all cases, the threshold of detection depends on the level of modification of the probe.

6.3 Capture and Detection of Double-stranded RNA Molecules.

After it was verified that it was possible to capture and detect a single-stranded RNA molecule on a microplate, the possibility of capture of double-stranded molecules was studied. In actual fact, the presence of a given mRNA in a sample is verified by hybridization with a riboprobe. The hybrid formed is protected from degradation by ribonucleases, whereas the single-stranded molecules are removed by digestion. The detection of hybrid molecules is hence the feature which discloses the presence of an mRNA. The double-stranded molecules studied contain a different percentage of modifications.

FIG. 3A shows the study of the binding of the riboprobes (5, 15, 25, 35% biotin-UTP) after formation of a hybrid with an ($\alpha$-$^{32}$P) CTP-radio labeled complementary ribonucleotide sequence. It should be noted that, in order to be able to monitor the behavior of the hybrid on plates, only the complementary strand is radiolabeled.

It is apparent that the optimum binding of the hybrid occurs at between 15 and 25% of biotin-UTP.

As for the single-stranded riboprobe, 5% of biotin-UTP is insufficient to bind the hybrid properly.

Figure 3B:
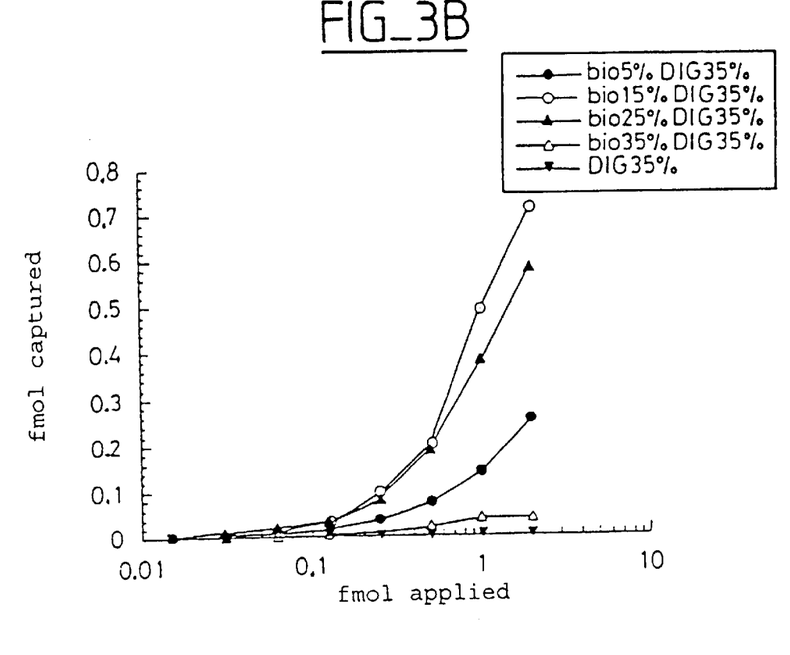
FIG. 3B depicts the capture of riboprobes (5, 15, 25, 35% biotin-UTP) hybridized with a ($\alpha$-$^{32}$P) CTP-labeled nucleotide sequence (35% DIG-UTP). This enables the binding of the riboprobes in double-stranded form to be studied. The detection of the hybrids is performed by measurement of the radioactivity.

FIG. 3B shows the influence of the degree of biotin-UTP on the capture of hybrid consisting of (5, 15, 25, 35%) biotin-UTP and 35% DIG-UTP.

The maximum capture of the biotin-UTP, DIG-UTP hybrid is obtained with 15% of biotin-UTP.

These results confirm those obtained above. Moreover, a probe containing 35% of biotin-UTP gives rise to a very low level of binding of the hybrid. Probably as a result of a lower stability of the duplex obtained in the presence of 35% DIG-UTP. This result demonstrates that an excessive modification of the riboprobe destabilizes the hybrid, and manifests itself in a very low level of capture.

It is also possible to detect double-stranded RNA molecules using anti-DIG antibodies coupled to alkaline phosphatase, followed by a measurement of fluorescence (results not shown).

Figure 4:
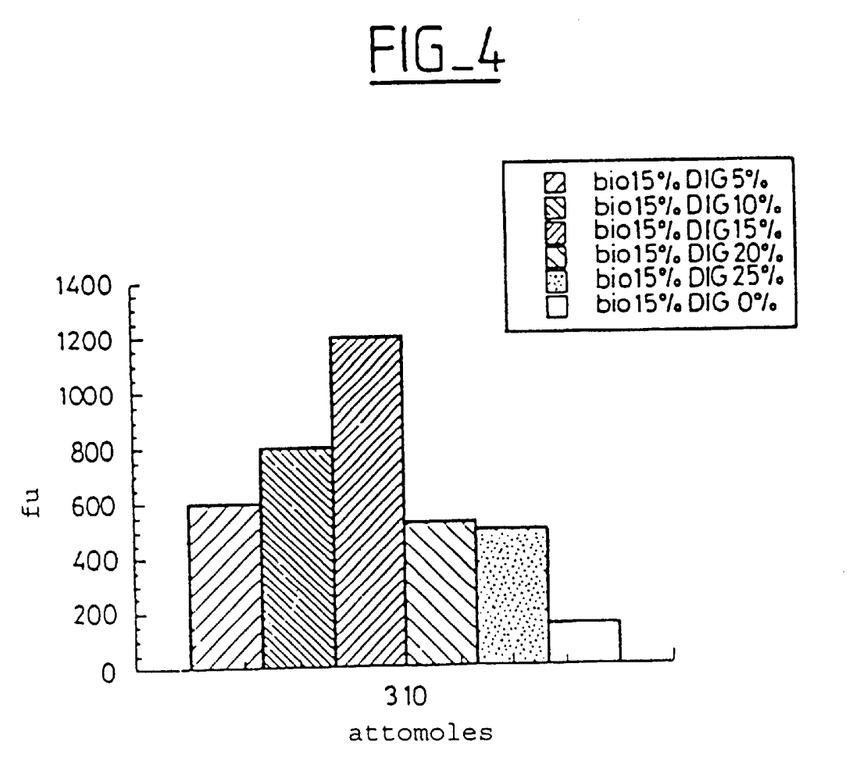
FIG. 4 shows the influence of the percentage of DIG-UTP on the size of the detection signal using anti-DIG antibodies. The probes studied consist of 15% biotin-UTP and (5, 15, 20, 25% of DIG-UTP)

For example, FIG. 4 demonstrates that optimum detection of the hybrid is achieved when the riboprobe containing 15% of biotin-UTP also contains 15% of DIG-UTP.

These results collectively indicate very good binding of the riboprobe containing 15% of biotin-UTP, in both single-stranded and double-stranded form.

The results obtained show the potential possessed by the biotin-UTP, DIG-UTP riboprobes (in single and double-stranded form) for binding to and being detected on microplates. These riboprobes possessing both capture and detection properties are seen to be very suited to a messenger RNA detection which can be automated. However, different plate-binding behavior between a single and double-stranded molecule was observed. For a single-stranded molecule, the degree of capture is linked directly to the amount of biotin-UTP incorporated in the riboprobe. Whereas for a double-stranded molecule, the degree of capture passes through an optimum which is reached when the riboprobe consists of 15% of biotin-UTP. Thus, for double-stranded molecules, the degree of binding is not directly correlated with the amount of biotin contained in the hybrid, but is a consequence of the stability of the hybrid and percentage of modification. This implies the need to perform an optimization of the binding of double-stranded molecules.

EXAMPLE 2

EFFECT OF THE INCORPORATION OF MODIFIED NUCLEODIDES IN A RIBOPROBE ON THE STABILITY TO DEGRADATION BY RIBONUCLEASES SPECIFIC FOR SINGLE STRANDS

Example 1 shows that an excessive proportion of modification brings about a destabilization of double-stranded RNAs. It is hence essential to determine the consequences of such modifications in relation to the test of protection from digestion with ribonucleases. Moreover, in this test, the pairing of the two strands of the hybrid has to be very stable, since any unpairing gives rise to a cleavage by the ribonucleases and a loss of the specific signal. On the other hand, since the modifications are located on the uridine, it is probable that the ribonucleases which cut at this nucleotide are less tolerant than those which cut after another nucleotide.

Different types of ribonuclease are available on the market (C13, T1, A, PhyM, U2). They have the common feature of only degrading an RNA molecule in single-stranded form and of leaving double-stranded molecules intact. These enzymes differ in the specificity of their cleavage sites.

Traditionally, the ribonuclease protection test is carried out.with a mixture of ribonucleases A and T1. However, it was verified that ribonuclease A, which cuts after uridine, cytidine and thymidine residues, is less usable than ribonuclease T1 which cuts only after guanosine (not shown). This made it possible to eliminate ribonuclease A from the test, and to retain only ribonuclease T1 which affords a better compromise between the preservation of the specific signal (double-stranded molecule) and the degradation of the non-specific (single-stranded) signal. In order to avoid the presence of a high background during visualization on microplates, it is necessary for the unhybridized probe to be completely digested.

1. Synthesis of the Probes

The synthesis of the HNF1 probes and antiprobes was carried out as for Example 1.

2. Hybridization

One fmol of HNF1 antisense probe containing different modifications (biotin and/or DIG) is hybridized with 10 and 1 ng of sense complementary sequences in the presence of 10 µg of yeast t RNA. The hybridization buffer consists of 40 mM PIPES pH 6.4; 1 mM EDTA pH 8.0; 0.4 M NaCl; 80% deionized formamide. After denaturation of the mixture at 93° C. for 4 minutes, hybridization is carried out aat 43° C. for 16 hours.

3. Protection From Digestion by RNase T1

Digestion with RNase T1 is carried out after hybridization in order to degrade the unhybridized riboprobe and mRNAs.

Digestion with RNase T1 is carried out by adding 300 µl of digestion buffer: 300 mM NaCl; 10 mM Tris-HCl pH 7.4; 5 mM EDTA pH 7.5; 20 U RNase T1 (Boehringer). Digestion of the unhybridized RNAs is carried out at 37° C. for 30 minutes. The RNase T1 is then inactivated using 20µl of 10% SDS solution and 10 µl of a proteinase K solution at a concentration of 10 mg/ml. The mixture is incubated for 30 minutes at 37° C. The hybrids are extracted with 400 µl of phenol/chloroform/isoamyl alcohol mixture (Amesco). After centrifugation at 12,000 rpm for 5 minutes, the upper phase is transferred to a fresh tube. The hybrids are precipitated in the presence of 200 µl of 4M ammonium acetate and 750 µl of absolute ethanol for 30 minutes at −20° C.

Depending on the protocol for analysis of the hybrids, the pellet is taken up:
- either in 10 µl of loading buffer comprising 80% formamide; 0.1% xylene cyanol; 0.1% bromophenol blue; 2 mM EDTA. The pellet is then analyzed on acrylamide gel under denaturing conditions,
- or in 100 µl of capture buffer: 1×PBS; 1% bovine serum albumin. The sample is subsequently analyzed after binding to a microplate coated with streptavidin (Boehringer).

4. Analysis on Polyacrylamide Electrophoresis Gel

After denaturation of the sample by heating to 93° C. for 4 minutes, it is subjected to electrophoretic migration at 40–45 V/cm in a denaturing gel containing 5% of polyacrylamide; 7M urea containing 1×TBE.

The radioactivity is detected by autoradiography. The size of the band corresponding to the riboprobe is determined by comparison with the migration of radiolabeled DNA fragments of known sizes.

5. Results

The tests were directed towards determining whether the capture (biotin) or detection (DIG) modifications of the riboprobe are compatible with the nuclease protection tests. The test used is a protection from digestion by RNase $T_1$, followed by a traditional analysis on electrophoresis gel under denaturing conditions. The size of the HNF1 riboprobe is 500 nucleotides.

Biotin-UTP (35% and 100%) riboprobes (results not shown) and DIG-UTP (5, 15, 20 and 35%) riboprobes (results depicted in FIG. 5) were tested.

It is apparent that the higher the percentage of modification, the less the riboprobe is usable in the ribonuclease protection test. Thus, it is not possible to use riboprobes consisting of 35% of biotin-UTP and 35% DIG-UTP since there is a complete loss of the specific signal due to degradation by the ribonucleases, probably as a result of the strains to which these modifications give rise in the hybrid. Likewise, 100% of UTP modification is not tolerated, irrespective of the modification (biotin-UTP, DIG-UTP).

Figure 5:
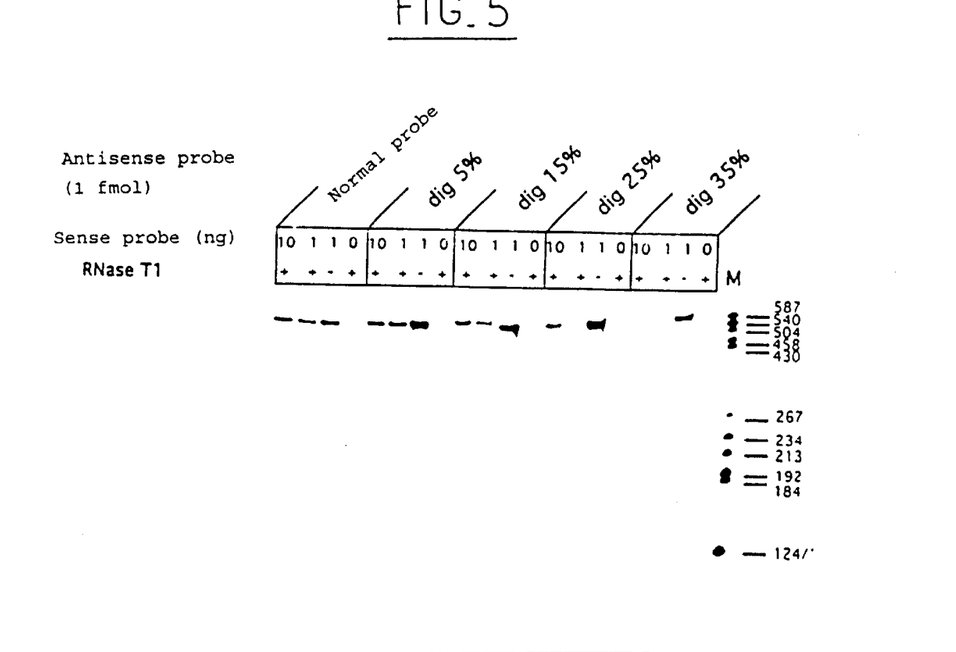
FIG. 5 shows the use of DIG-UTP riboprobes in a functional test of nuclease protection.

Fine analysis of the degradation of the hybrid as a function of the percentage of DIG-UTP incorporated in the riboprobe discloses that an increase in the degree of modification gives rise to a progressive loss of sensitivity. The maximum threshold of DIG-UTP modification without significant loss of specific signal is obtained with a probe containing 10% of DIG-UTP (FIG. 5).

Figure 6:
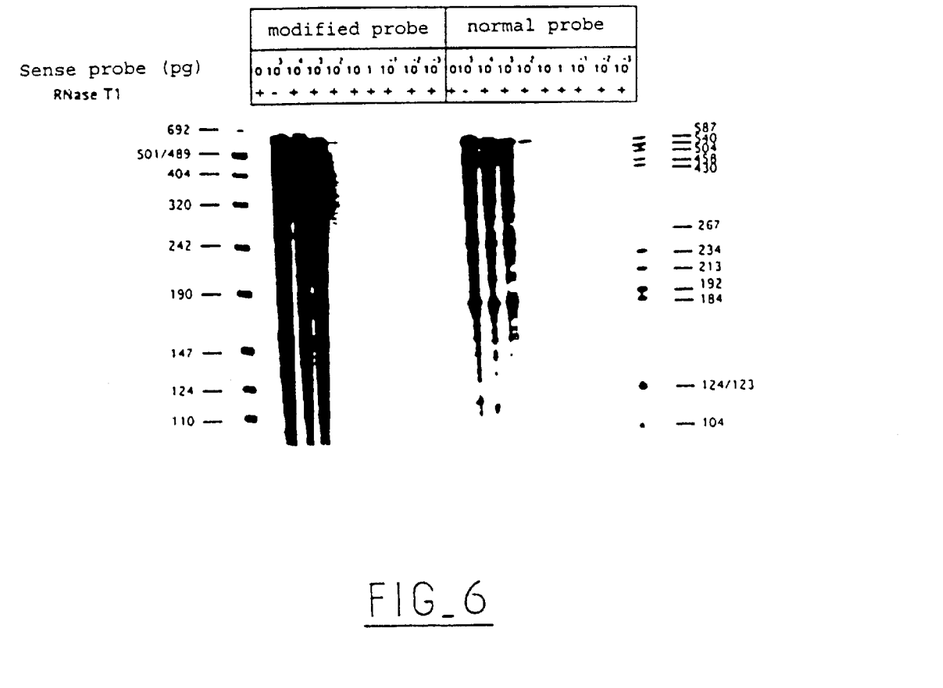
FIG. 6 depicts the autoradiograph of a polyacrylamide gel, and shows the sensitivity of detection using a radiolabeled riboprobe consisting of 15% of biotin-UTP and 10% of DIG-UTP compared to the same radiolabeled riboprobe unmodified.

FIG. 6 shows a comparative study of sensitivity between a riboprobe (15% biotin-UTP, 10% DIG-UTP) and the same riboprobe unmodified. The test used is a protection from digestion by Rnase T1, followed by a traditional analysis on electrophoresis gel under denaturing conditions. In this experiment, both radiolabeled riboprobes possess a specific activity of $4 \times 10^4$ cpm per fmol. The riboprobe (15% biotin-UTP, 10% DIG-UTP) is capable, like the unmodified probe, of detecting 100 pg of complementary sequence, but with a weaker signal.

These results show that, in the case of the use of biotin as capture modification and DIG in detection, 15% of biotin and 10% of DIG appear to be suitable for a good detection of the target RNAs. With other modifications, it will be necessary to carry out an optimization.

EXAMPLE 3

USE OF A RIBOPROBE (15% BIOTIN-UTP, 10% DIG-UTP) FOR DETECTING THE MESSENGER OF THE b-ACTIN OR HNF1 GENE ON MICROPLATES

The synthesis of the HNF1 riboprobe, capture and detection were carried as for Example 1.

1. Synthesis of the β-actin Probe

A 250-bp fragment of a cDNA coding for mouse β-actin (582-831) is cloned at the KpnI/XbaI site of the vector pBS (Stratagene). The β-actin riboprobe is obtained after linearization of the vector by cleavage with HindIII followed by a transcription with T7 RNA polymerase.

2. Extraction of the Total RNAs

The total RNAs are isolated from $10^7$ cells or from 10 to 100 mg of tissues using 2 ml of RNAzol B (Biotex). The tissue has to be plunged frozen into the RNAzol B, and homogenization is carried out in a "waring blender" mill for 30 to 60 seconds before the tissue thaws, otherwise the RNAs will be degraded by the Rnases. 0.2 ml of chloroform is then added to the homogenate. After being mixed and left standing for 5 minutes in ice, the solution is centrifuged at 12,000 g for 15 minutes at 4° C. After the aqueous phase has been removed, an equal volume of isopropanol is added. The mixture is allowed to precipitated at −20° C. for 30 minutes. After centrifugation at 12,000 g for 15 minutes at 4° C., the pellet is washed with 70% alcohol. The total RNAs are resuspended in DEPC water. The concentration of the sample is determined by measuring the optical density at 280 nm. The quality of the preparation is verified on 0.8% agarose gel.

3. Hybridization

The amount of total RNAs needed for the hybridization reaction depends on the concentration of the nucleotide sequence which is sought and the specific activity of the radiolabeled riboprobe. With a riboprobe having a high specific activity (>$10^9$ cpm/μg), 10 μg of total RNAs are usually sufficient to permit the detection of mRNAs which are present at a level of 1 to 5 copies per cell.

The total RNAs (10 μg) to be analyzed are precipitated by adding 0.1 volume of 3 M sodium acetate solution ph 5.2 and 2.5 volumes of cold ethanol. The solution is left for 30 minutes at −20° C. The tRNAs are recovered by centrifugation at 12,000 rpm for 15 minutes at 4° C. The pellet is then washed with 70% ethanol solution and recentrifuged. After removal of the ethanol, the pellet is dried. The tRNAs are then dissolved in 20 ml of hybridization buffer containing: 40 mM PIPES pH 6.4; 1 mM EDTA pH 8.0; 0.4 M NaCl; 80% deionized formamide. 1 fmol of the biotin-DIG riboprobe, radiolabeled or otherwise, is then added. The solution is pipetted several times to permit complete solubilization of the pellet. The mixture is denatured by incubation at 93° C. for 4 minutes. The tubes are then transferred rapidly to a water bath adjusted to the hybridization temperature. In most cases, satisfactory results are obtained when the RNAs are hybridized at between 45 and 50° C. for 16 hours.

4. Results

Figure 7:
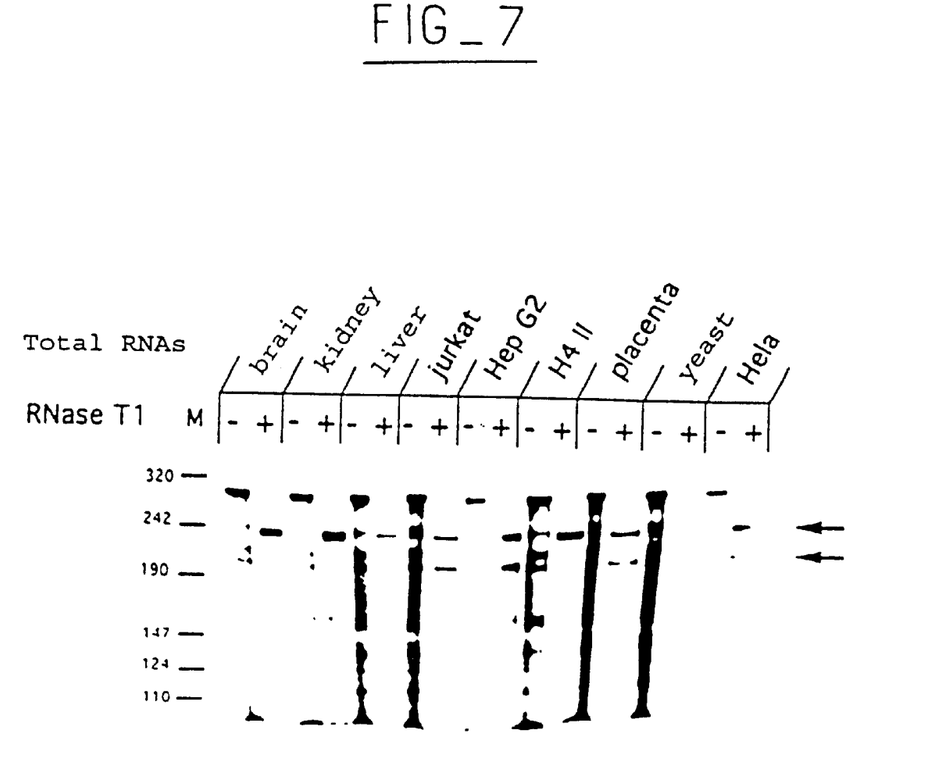

FIG. 7 shows the use of a riboprobe (15% biotin-UTP, 10% DIG-UTP, ($\alpha$-$^{32}$P) CTP) corresponding to a sequence complementary to the mouse β-actin messenger. The size of the riboprobe is 250 base pairs.

The riboprobe (15% biotin-UTP, 10% DIG-UTP, ($\alpha$-$^{32}$P) CTP was capable of detecting the β-actin messenger in 10 μg of total RNAs. The test used is a protection from digestion by Rnase T1 followed by analysis by acrylamide gel electrophoresis under denaturing conditions. The size integrity of the ribonprobe is determined as a result of the presence of radiolabeled markers.

The riboprobe is seen to be protected in all the samples tested (see arrow in FIG. 7). However, for the human samples, the presence of a second band of smaller size (arrow), which is due to the existence of a difference in the sequence of the b-actin gene between man and mouse in respect of an Rnase T1 cleavage site, should be noted. The β-actin messenger was visualized in all the cells tested. The specificity of the detection is given by yeast, which does not express β-actin.

This demonstrates that the riboprobe (15% biotin-UTP, 10% DIG-UTP) pairs correctly with a complementary sequence located in an mRNA. And that it can hence be used in the functional tests of protection from digestion by RNase T1.

Figure 8:
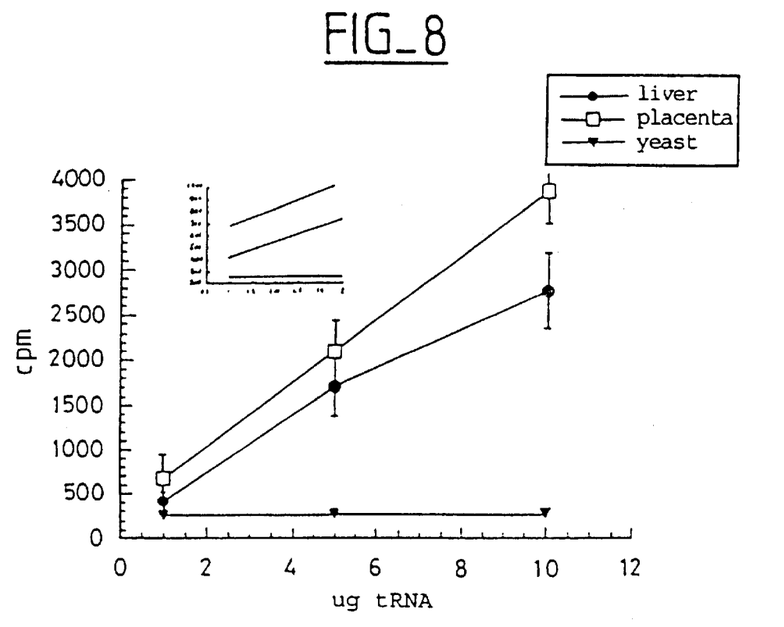
FIG. 8 depicts a detection on plates (after protection from digestion by ribonuclease T1) of the $\beta$-actin messenger with a riboprobe consisting of 15% of biotin-UTP and 10% of DIG-UTP, radiolabeled with ($\alpha$-$^{32}$p) CTP ($3 \times 10^4$ cmp/fmol).

FIG. 8 shows the results obtained after protection from digestion by Rnase T1 followed by detection of the radioactivity after capture on microplates. The same amount of β-actin riboprobe (15% biotin-UTP, 10% DIG-UTP), 1 fmol ($4\times10^4$ cpm), was used for the detection on gel and on plates. As in the analysis using polyacrylamide electrophoresis gel, the riboprobe (15% biotin-UTP, 10% DIG-UTP, ($\alpha$-$^{32}$p) CTP is capable of detecting the presence of the β-actin messenger starting from 1 μg of total RNAs. The yeast used as negative reaction control gives a very low background (250 cpm), compared to the 1800–4000 cpm obtained with 5 and 10 μg of tRNA from cells expressing β-actin. Although much weaker (400–680 cpm), the signal remains positive with 1 μg of tRNA.

Figure 9:
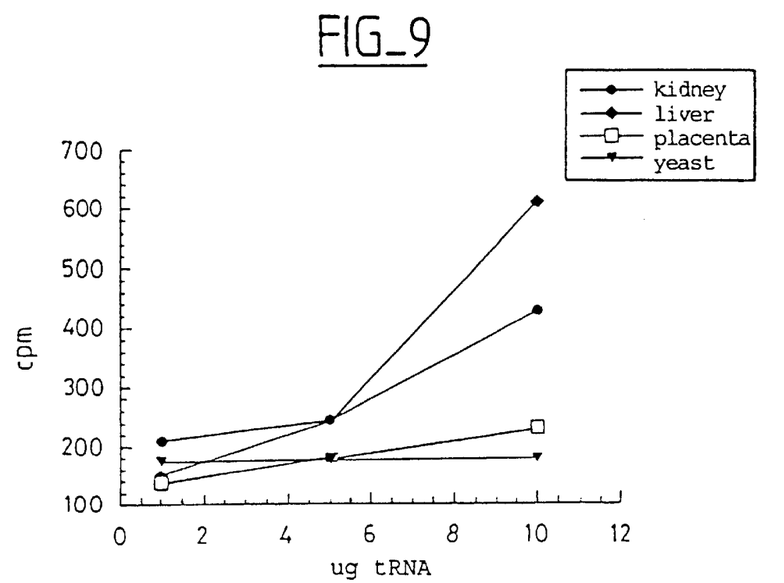
FIG. 9 depicts a detection on plates of an uncommon messenger, that of HNF1 (hepatic nuclear factor 1) using a riboprobe (15% biotin-UTP, 10% DIG-UTP) radiolabeled with $\alpha$-$^{32}$P-CTP ($5 \times 10^4$ cpm/fmol). The samples tested correspond to 10, 5 and 1 $\mu$g of tRNA originating from kidney, liver, placenta and yeast.

FIG. 9 shows the results obtained with a riboprobe (500 nucleotides) directed against a weakly expressed messenger, that of HNF1. The probe used, containing 15% of biotin-UTP and 10% of DIG-UTP, is radiolabeled with ($\alpha$-$^{32}$P) CTP ($5\times10^{5^5}$ cpm/fmol). The measurement of the radioactivity associated with the two cells that express HNF1 (kidney and liver) is significantly higher than that associated with the samples which do not express HNF1 (placenta and yeast). This result demonstrates the possibility of detection by a riboprobe (biotin-UTP, DIG-UTP) of a weakly represented mRNA.

However, in order to be completely amenable to automation, this method of analysis on microplates has to dispense with the use of radioactivity.

Figure 10:
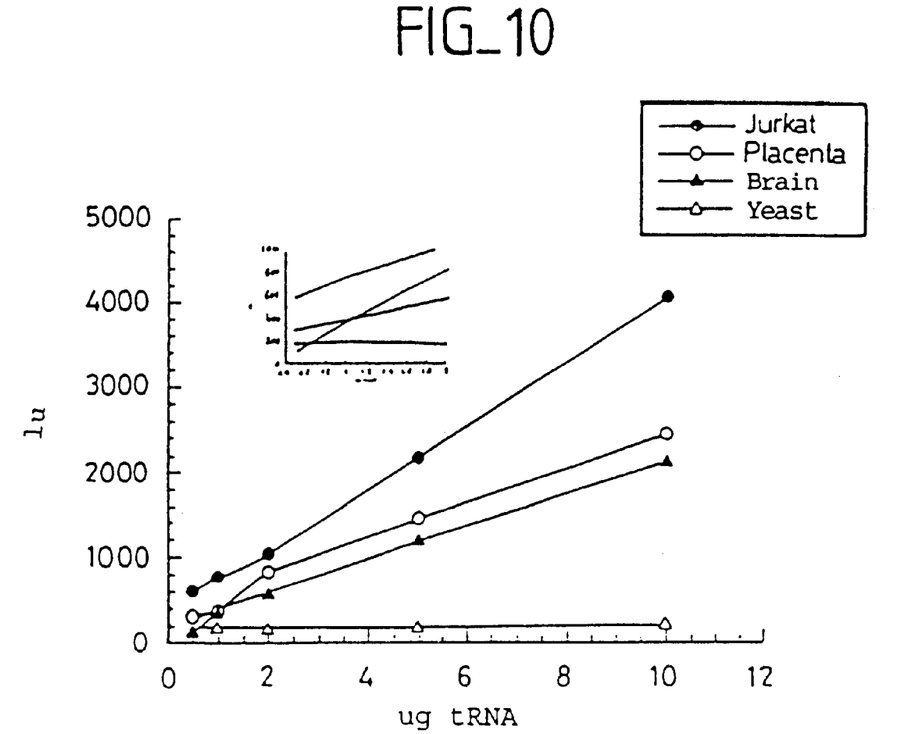
FIG. 10 depicts a detection on plates of the $\beta$-actin messenger with a riboprobe consisting of 15% of biotin-UTP and 10% of DIG-UTP. The detection of the riboprobe is carried out using an anti-DIG antibody coupled to alkaline phosphatase. The measurement is carried out by luminescence.

FIG. 10 shows the results obtained with a β-actin riboprobe (15% biotin-UTP, 10% DIG-UTP), followed by detection on microplates with an anti-DIG antibody and a reading by luminescence.

The cells tested are: Jurkat, placenta, brain, yeast.

From Jurkat cells, it was possible to detect the β-actin messenger in 0.5 μg of tRNA. For placenta and brain, the β-actin messenger was demonstrated in 2 μg of tRNA. These results indicate the very good sensitivity of the detection method.

As when using radioactivity, the riboprobe is capable of detecting the β-actin messenger starting from 10, 5, 2 or 0.5 μg of total RNAs.

Similar results are obtained with fluorescent detection (not shown).

These studies collectively show that the riboprobes (biotin-UTP, DIG-UTP), while retaining their specificity of recognition via their ribonucleotide sequences, are capable of binding to plates and being detected specifically. Their use in nuclease protection tests necessitated an adjustment of the degree to which they were modified.

Although the nuclease protection technique is frequently used in mRNA detection and quantification studies. It nonetheless remains unsuitable for the analysis of large series of samples. Since the products of nuclease protection experiments are usually analyzed on polyacrylamide gel under denaturing conditions. The possibility of detecting messenger RNAs on microplates using a riboprobe (biotin-UTP, DIG-UTP) constitutes a tool of very great analytical power, and makes the nuclease protection technique applicable to the study of large numbers.

What is claimed is:

1. A method for detecting nucleic acids comprising the following steps:
   a) performing a hybridization reaction in solution using a nucleic acid probe capable of hybridizing with a given RNA or DNA in a sample containing nucleic acids, said probe comprising detection components and first capture components;
   b) degrading the unhybridized nucleotide sequences in the sample with an enzyme that degrades unhybridized nucleic acids;

c) capturing hybrids comprising said nucleic acid probe and said RNA or DNA by bringing them into contact with a solid support comprising second capture components that interact with said first capture components of said probe;

d) detecting the hybrids, or the probes originating from the hybrids after denaturation, by means of said detection components.

2. The method of claim 1, wherein said nucleic acid probe is an RNA probe and wherein the enzymatic degradation is carried out with an RNase.

3. The method of claim 1, wherein said first capture components of said probe comprise a first biological molecule bound covalently to said probe and said second capture components of said solid support comprise a second biological molecule bound to the solid support, which second biological molecule interacts and binds noncovalently to said first molecule.

4. The method of claim 1 wherein said RNA or DNA comprises an mRNA and said probe comprises an RNA probe obtained by in vitro transcription of cloned cDNA fragments, said cDNA fragments being derived from said mRNA.

5. The method of claim 1, wherein said probe is from 100 to 1000 nucleotides in length.

6. The method of claim 1, wherein after step b), the degradation products of the unhybridized nucleic acids are removed.

7. The method of claim 1, wherein said probe does not contain more than 15% of nucleotides modified with said detection components and wherein said first capture components comprise biological molecules.

8. The method of claim 3, wherein said first and second capture molecules comprise a biotin/streptavidin system.

9. The method of claim 3, wherein said first capture molecule is digoxigenin (DIG) and said second capture molecule is an anti-digoxigenin antibody.

10. The method of claim 1, wherein said detection component is a directly detectable radioactive or fluorescent component.

11. The method of claim 1, wherein said detection component is an indirectly detectable component comprising a biological molecule capable of reacting noncovalently with another molecule containing a directly detectable component.

12. The method of claim 11, wherein the indirectly detectable detection component is selected from the group consisting of biotin, fluorescein and digoxigenin.

13. The method of claim 1, wherein said first capture component is selected from the group consisting of biotin, fluorescein and digoxigenin.

14. The method of claim 1, wherein the detection component is digoxigenin and/or biotin and said first capture component is selected from the group consisting of biotin and digoxigenin, respectively.

15. The method of claim 14, wherein from 2 to 5% of the nucleotides in said probe are substituted with a biotin molecule and from 2 to 5% of the nucleotides in said probe are substituted with a digoxigenin molecule.

16. The method of claim 1, wherein said probe is from 250 to 500 nucleotides in length.

17. The method of claim 1, wherein said probe does not contain more than 10% of nucleotides modified with said detection components and wherein said first capture components comprise biological molecules.

18. The method of claim 14, wherein from 3 to 4% of the nucleotides in said probe are substituted with a biotin molecule and wherein from 2 to 3% of the nucleotides in said probe are substituted with a digoxigenin molecule.

19. The method of claim 4, wherein said in vitro transcription is performed using nucleotides having said detection component and/or said first capture components linked thereto.

20. The method of claim 1, wherein said step of degrading the unhybridized nucleotide sequences comnrises preferentially cutting the unhybridized nucleotide sequences at nucleotides other than those which comprise said detection components and/or said first capture components.

21. The method of claim 20 wherein said detection components and said first capture components are linked to uridines in said probe and wherein said enzyme that degrades unhybridized nucleic acids comprises RNase $T_1$.

22. The method of claim 1, wherein said RNA or DNA comprises an RNA or DNA associated with a pathology.

23. The method of claim 1, wherein said hybrids or probes are detected without performing gel electrophoresis or size exclusion chromatography.

24. A kit comprising a nucleic acid probe comprising detection components and first capture components and a solid support comprising second capture components, said second capture components being capable of binding specifically with said first capture components, wherein said first and second capture components comprise a ligand-receptor or an antigen-antibody system and said detection components and said capture components are different and distinct molecules.

25. The kit of claim 24, wherein said probe is more than 100 nucleotides in length.

* * * * *